(12) United States Patent
Montejo

(10) Patent No.: US 9,517,087 B2
(45) Date of Patent: Dec. 13, 2016

(54) BONE FIXATION SYSTEM AND METHODS

(71) Applicant: Javier Montejo, Neiva (CO)

(72) Inventor: Javier Montejo, Neiva (CO)

(*) Notice: Subject to any disclaimer, the term of this patent is extended or adjusted under 35 U.S.C. 154(b) by 0 days.

(21) Appl. No.: 14/835,220

(22) Filed: Aug. 25, 2015

(65) Prior Publication Data

US 2015/0351801 A1  Dec. 10, 2015

Related U.S. Application Data

(63) Continuation-in-part of application No. PCT/IB2014/066210, filed on Nov. 20, 2014, and a continuation-in-part of application No. 13/846,980, filed on Mar. 19, 2013, now abandoned.

(51) Int. Cl.

| | |
|---|---|
| *A61B 17/58* | (2006.01) |
| *A61B 17/68* | (2006.01) |
| *A61B 17/86* | (2006.01) |
| *A61C 8/00* | (2006.01) |
| *A61C 7/36* | (2006.01) |
| *A61B 17/66* | (2006.01) |
| *A61B 17/64* | (2006.01) |

(52) U.S. Cl.
CPC ......... *A61B 17/683* (2013.01); *A61B 17/6433* (2013.01); *A61B 17/663* (2013.01); *A61B 17/864* (2013.01); *A61B 17/8605* (2013.01); *A61C 7/36* (2013.01); *A61C 8/0096* (2013.01)

(58) Field of Classification Search
CPC ................ A61B 17/663; A61B 17/864; A61C 7/12–7/36
See application file for complete search history.

(56) References Cited

U.S. PATENT DOCUMENTS

| | | | |
|---|---|---|---|
| 2,502,902 A | 4/1950 | Tofflemire | |
| 4,090,299 A | 5/1978 | Williams | |
| 4,431,409 A * | 2/1984 | Picard | A61C 7/146 433/2 |
| 4,797,095 A | 1/1989 | Armstrong et al. | |
| 5,087,202 A | 2/1992 | Krenkel | |
| 5,158,452 A * | 10/1992 | Franseen | A61C 7/12 433/24 |
| 5,839,899 A | 11/1998 | Robinson | |
| 5,842,856 A | 12/1998 | Casey | |

(Continued)

FOREIGN PATENT DOCUMENTS

WO  2012046888 A1  4/2012

*Primary Examiner* — Nicholas Plionis
(74) *Attorney, Agent, or Firm* — St. Onge, Steward, Johnston & Reens

(57) ABSTRACT

An intermaxillary fixation system is provided, including a bone anchorage screw having at least one of an elongated head with internal threading and an externally threaded screw extending from a head of the bone anchorage screw, a fixation system, and a rail bar. A method for the stabilization and fixation of maxillary and mandibular arches is also provided, including setting a plurality of bone anchorage screws to the maxillary and mandibular arch, each bone anchorage screw having a head, fixing one or more T-shaped bars to the bone anchorage screws, bending and connecting a rail bar to heads of the one or more T-shaped bars with orthodontic screws, and wrapping a connector between the heads of the bone anchorage screws located on the mandibular arch and the maxillary arch.

10 Claims, 4 Drawing Sheets

(56) References Cited

U.S. PATENT DOCUMENTS

| | | | |
|---|---|---|---|
| 5,954,502 A * | 9/1999 | Tuenge | A61C 7/14 433/16 |
| 6,086,365 A | 7/2000 | Fields | |
| 6,227,861 B1 | 5/2001 | Cartledge et al. | |
| 6,257,884 B1 | 7/2001 | Chang | |
| 6,595,774 B1 | 7/2003 | Risse | |
| 6,827,574 B2 | 12/2004 | Payton | |
| 7,281,923 B1 * | 10/2007 | DeVincenzo | A61B 17/8061 433/173 |
| 7,351,058 B2 | 4/2008 | Fore et al. | |
| 7,931,469 B1 | 4/2011 | Schendel | |
| 2001/0018176 A1 | 8/2001 | Branemark | |
| 2002/0013586 A1 | 1/2002 | Justis et al. | |
| 2002/0143336 A1 | 10/2002 | Hearn | |
| 2002/0150856 A1 | 10/2002 | Payton | |
| 2003/0160552 A1 | 8/2003 | Bacho et al. | |
| 2004/0086824 A1 | 5/2004 | Kesling | |
| 2004/0147931 A1 | 7/2004 | De Clerck | |
| 2004/0152046 A1 | 8/2004 | Minoretti et al. | |
| 2004/0166461 A1 | 8/2004 | Devincenzo | |
| 2005/0059971 A1 | 3/2005 | Michelson | |
| 2005/0130092 A1 * | 6/2005 | Minoretti | A61B 17/663 433/7 |
| 2005/0142513 A1 | 6/2005 | Hotta | |
| 2005/0147938 A1 | 7/2005 | Devincenzo et al. | |
| 2005/0261690 A1 | 11/2005 | Binder et al. | |
| 2005/0282115 A1 | 12/2005 | Gedebou | |
| 2006/0069389 A1 | 3/2006 | Knopfle | |
| 2006/0078849 A1 | 4/2006 | Parks | |
| 2007/0259306 A1 | 11/2007 | Raines, Jr. et al. | |
| 2008/0138759 A1 * | 6/2008 | Kravitz | A61C 7/00 433/21 |
| 2008/0254401 A1 | 10/2008 | Yazdi | |
| 2009/0170050 A1 | 7/2009 | Marcus | |
| 2011/0288596 A1 | 11/2011 | Brand et al. | |
| 2012/0214120 A1 | 8/2012 | Marcus | |
| 2013/0244193 A1 | 9/2013 | Yu et al. | |
| 2014/0272754 A1 * | 9/2014 | Curley | A61C 7/287 433/11 |

* cited by examiner

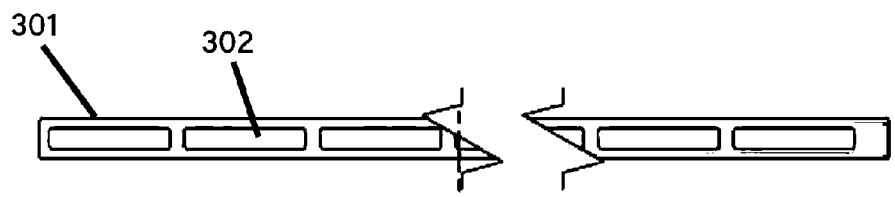
FIG. 3
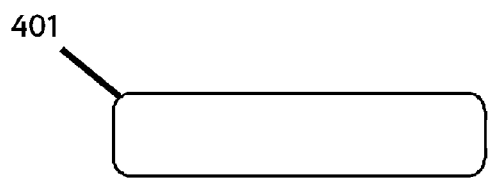
FIG. 4
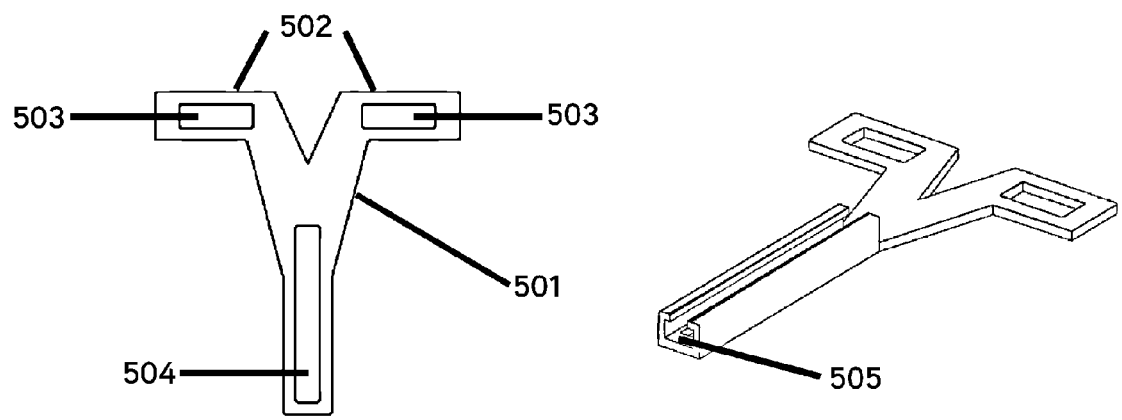
FIG. 5A
FIG. 5B

US 9,517,087 B2

BONE FIXATION SYSTEM AND METHODS

FIELD OF THE INVENTION

The present invention relates, in general, to the fixation of bone fractures, and more particularly to maxillary or mandibular stabilization or reduction of any possible fractured bone fragments.

The present invention also relates to the fixation of bone fractures in orthodontic circumstances where there is a need for bone space in order to perform dental movements.

BACKGROUND OF THE INVENTION

Within the field of oral and maxillofacial surgery one of the most important phases in the handling of fractures is intermaxillary fixation (IMF), due to the fact that during this step, the patient's original occlusion is reestablished.

Historically, intermaxillary fixation systems have been based on the use of teeth as anchorage for interdental surgical wires such as Erich, Ivy or Kazanjian arch bars, which are used in procedures that require maxillary fracture reductions. Notwithstanding their functionality, these systems have a number of disadvantages for both patient and surgeon, being the health of the gums the main issue at hand after their prolonged use.

For the patient, these systems cause discomfort and ailments in cases when the injuries are reversible, and when irreversible, they can produce grave periodontal disease. For the surgeon, these fixation systems require the existence of intact teeth in order to perform the procedure, a situation that is often difficult when faced with severe fractures. Additionally, their troublesome wire-based installation represents a biological hazard.

During the last twenty years, a solution to these problems has been presented with the appearance of IMF bone screws that have allowed for a rapid intermaxillary fixation. These screws are placed through the gingival and into the bone, leaving a protruding head. A wire is then attached between two or more screw heads in order to secure the IMF.

This system, however, has disadvantages. For example, it does not provide sufficient stability to the fixation, producing posterior open bites. Additionally, bone fragments can be twisted upon tightening the wires, they cannot provide a tension band effect, and they cannot be used for fractures between teeth or when post treatment requires the use of elastic IMF. Furthermore, their installation is difficult in complex traumas.

Most recently, a hybrid system has appeared on the market that utilizes both the utility of an arch bar as an IMF device, and the fixation of this bar using IMF self-tapping bone screws to connect it to the maxillary and mandibular arch. This device does provide for modular placement of the IMF bone screws, but carries the same disadvantages of the arch bar and bone screws of the prior art systems. The system has a plurality of hooks that sustain a wire or elastic, an arch bar that is laid upon the gums (making cleanliness difficult), and the placement of IMF self-tapping bone screws between the roots of teeth (potentially causing root and nerve damage).

Within the field of orthodontics, there are cases in which teeth may not be used as an anchorage point. In these cases, it is necessary to use bone anchorage in order to perform dental movements. Bone fixation systems in orthodontics have been historically based on the use of mini implants or screws with different devices on their heads, such as perforations allowed for the use of wires or elastic bands. More recently, some commercial brands have started implementing bone fixation systems made up of mini plates that are fixed to the bone. Notwithstanding their functionality, these systems have a number of disadvantages for both patient and surgeon. In the case of the traditional screw mechanism, their placement is the most inconvenient due to the location of the tooth apex. Regarding the mini plates systems, their biggest surgical difficulty lies in the difficulty of their insertion.

For the patient, these systems can damage the dental roots due to their proximity to the screws. For the surgeon, the biggest inconvenience is the high level of difficulty of locating the screws in possible and limited spaces without altering the anatomy and physiology of the bone and the tooth.

In all of these cases, the use of a less invasive system can avoid these inconveniences.

SUMMARY OF THE INVENTION

The system of the present invention is innovative because it does not use teeth as an anchorage point, thereby reducing periodontal disease and improving the stability of the IMF. The system distances itself from possible alveolus bone engagement, thereby preventing possible nerve or root damage.

The invention comprises a bone fixation and/or orthodontic realignment system that utilizes a bone anchorage screw with internal threading for receiving an orthodontic screw or rail bar orthodontic screw. In additional embodiments, a bone anchorage screw is used with an additional externally threaded screw extending from its head that can be set using either a nut or capped nut. The invention further comprises a T-shaped orthodontic bar, a flexible rail bar with rounded edges, or C-shaped flexible rail bar with an internal space for accommodating nuts. The figures discussed below show, collectively, an adaptable and easily customizable system for particular uses, such as for fracture reduction, intermaxillary fixation, or for dental realignment.

The invention also provides a set of linking materials, such as wires, elastic bands or plastic straps, used for the intermaxillary fixation.

BRIEF DESCRIPTION OF THE DRAWINGS

FIG. 3 is a top view of one exemplary embodiment of a rail bar (301).

FIG. 4 is an end view of a rail (301) bar of FIG. 3.

FIG. 5A is a top view of a T-shaped orthodontic bar (501) with a head (502) and a bottom (504) portion.

FIG. 5B is a top isometric view of the T-shaped orthodontic bar of FIG. 5A with a C-shaped rail on the bottom portion (505).

DETAILED DESCRIPTION OF THE INVENTION

Figure 1:
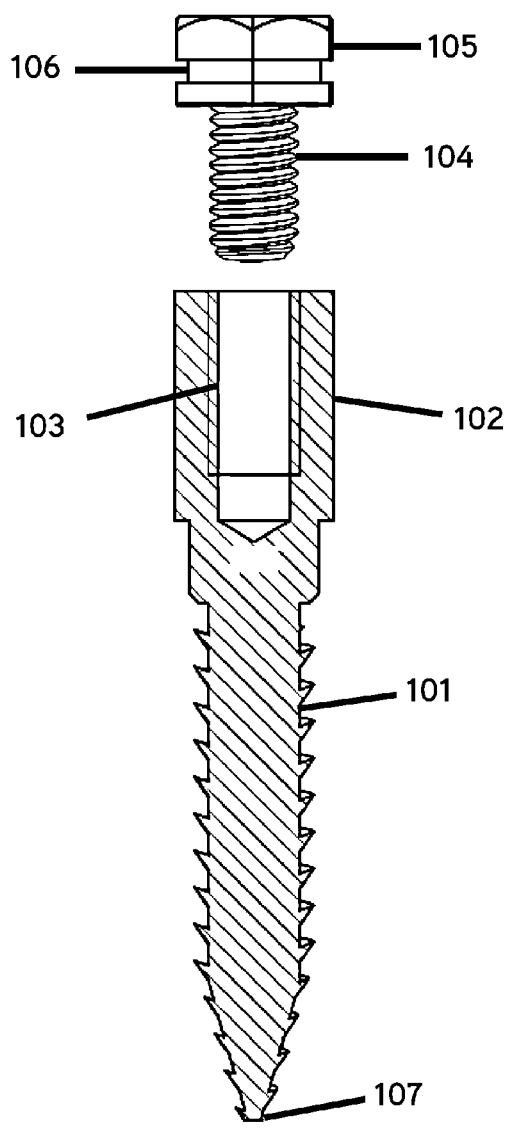
FIG. 1 is a side and cross-sectional view of one exemplary embodiment of a bone anchorage screw (101) and accompanying screw (104).

The following describes one manner in which the invention is to be performed. However, it should be understood that these described embodiments do not limit the inventive concept of the technology, and it is written for the best comprehension of the technology's essential components.

An object of the present invention is to provide a bone anchorage system comprising a smooth flexible rail laminate (301) with rounded edges anchored to the maxillary bone, secured through the use of a tiered bone screw (101) and T-shaped bar (501) that, once installed, works for IMF through the use of additional linking materials (801) such as bars, wires, elastics or plastic straps. The present invention also allows for positioning orthodontic anchorage systems at any point on the bar through the use of screws placed on the rail bar or an extension system on the occlusal plane, as is proposed with the T-shaped bar (501).

In one exemplary embodiment, one or more bone anchorage screws (101) with optional hexagonal heads (102) are inserted into patient's bone tissue. The opening (504) at the bottom of the T-shaped bar (501) is set over the head of the bone anchorage screw (101) and is fixed with an orthodontic screw (104) comprised of a laterally indented optionally hexagonal head (105) of the same size as the head (102) of the bone anchorage screw (101). After four T-shaped bars (501) have been set on the maxilla or mandible and have been fixated with the head (502) of the T-shaped bars (501) in a linear alignment with the other Ts (501), a smooth rail bar (301) with rounded edges is bent and placed over the heads (502) of the T-shaped bars (501) and fixated on each side of the head (502) of the T-shaped bar (501) using orthodontic screws (104) with a lateral indentation in the optionally hexagonal head (105) and set with nuts (205) on the underside using a small wrench or pliers. Orthodontic screws (104) may then be placed on the maxillary and mandibular rails, fixed from behind with a nut (205), and then connected using linking materials (801) such as wire, elastic, or another material.

In some embodiments, the bone anchorage screw (101) is comprised of a self-tapping screw (107) on one end for insertion in bone tissue and a flat-headed, externally threaded screw (202) extending from the optionally hexagonal center, allowing for a nut (205) to be attached such that it may be fixated through an opening (504) in the bottom of a T-shaped bar (501).

In another embodiment, the T-shaped bar (501) has a C-shaped rail bar on the bottom (505) and the flat-headed, externally threaded screw (202) is passed through the opening (505) and is secured above the short horizontal extensions at the top of the C-shaped rail with a cap nut (206) or nut (205).

In another embodiment, a smooth flexible rail bar (301) with rounded edges can be bent and fixed to the bone anchorage screw (101) with either an internally (103) or externally (202) threaded head. In other embodiments, wire, plastic, elastic or other linking materials (801) may connect the superior and inferior rail bars (301) without the additional support of an orthodontic screw (104). In addiitonal embodiments, another rail bar (301) may be placed over the rail bars (301) fixed to the bone anchorage screws (101) on both the maxilla and mandible and set using orthodontic screws (104) and nuts (205).

In another aspect, a method of reducing a fracture is made by placing a wire around the head of two bone anchorage screws (101) placed on each side of the fracture and tightening until the fracture is reduced. The bottom of the T-shaped bar (504) should be fixed to each bone anchorage screw (101) and a rail bar (301) should be placed over the head (502) of the T-shaped bar (501) and fixed using an orthodontic screw (104) with a lateral indentation (106) in the optionally hexagonal head placed through each slot (503) on the sides of the head (502) of the T-shaped bar (501) and set using a nut (205) on the underside. The wire is then cut and the T-shaped bar (501) and rail bar (301) maintain rigidity.

In some embodiments, a rail bar (301) may be set over the bone anchorage screw (101) with external (202) or internally (303) threaded head after a wire (801) has been placed and tightened and fixed using an orthodontic screw (104) head or a nut (205), depending upon the type of bone anchorage screw (101) used.

In another aspect, a C-shaped rail bar (601) with vertical walls and a short horizontal internal extensions at the top of the walls can be bent and set to a bone anchorage screw (101) with externally threaded head (202) which is then fixed to the C-shaped rail bar (601) with a nut (205) set above the short horizontal extensions. Modular extensions like an orthodontic screw (104) or T-shaped bar (501) can be attached to this C-shaped rail bar (601) by sliding nuts (205) into the space between the flat bottom and the short horizontal extensions at the top prior to placing and fixing the bone anchorage screws (101). Screws are placed between the two sides of the short horizontal extensions at the top and are screwed into the nut (205) inside the rail, fixating the screw and if any, a modular extension. Orthodontic screws (104) may then be placed on the maxilla and mandibular rails, fixed with a nut (205), and then connected using wire, elastic, or another linking material (801).

In some embodiments, T-shaped bars (501) may be first fixed to the bone anchorage screws (101) and the C-shaped rail bar (601) may be placed over the heads (502) of the T-shaped bars (501) in order fixate a bar over the teeth. In other embodiments, wire, plastic, elastic or other linking materials (801) may connect the superior and inferior rail bars (301) without the additional support of an orthodontic screw (104). In additional embodiments, another rail bar (301) may be placed over the rail bars (301) connected to the T-shaped bars (501) that are fixed to the bone anchorage screws (101) on both the maxilla and mandibular and set using orthodontic screws (104) and nuts (205).

In another aspect, in the case of emergency mandibular fractures, bone anchorage screws (101) may be placed through the skin in the mandible with the flexible rail bar (301) with rounded edges set to the screws using a nut (205) or an orthodontic screw (104), depending on the type of bone anchorage screw (101), thereby acting as an external fixation device.

In some embodiments, one or more orthodontic screws (104) may be placed on each of the rail bars (301) and fixed using wire, plastic, elastic or other linking materials (801) to secure the IMF. In other embodiments, another rail bar (301) may be placed over the rail bars (301) fixed to the bone anchorage screws (101) on both the maxilla and mandibular and set using orthodontic screws (104) and nuts (205).

In another aspect, the rail bar—flat (301) or with vertical sides (601)—can be fixed to two or more bone anchorage screws (101) with a nut (205) or fixating screw (104) depending upon the style of the screw (101). Then an orthodontic screw (104) can be set into the rail bar (301) with a nut (205), allowing for a band of elastic, wire, or other linking material (801) to be connected to a tooth brace for the purpose of realigning malocclusions.

In some embodiments, the head (502) of the T-shaped bar (501) may be set to the rail bar (301) with orthodontic screws (104) and an orthodontic screw (104) may be placed at any position within the slot (504) at the bottom of the T-shaped bar (501). A band of elastic, wire, or other linking material (801) may be connected from the orthodontic screw (104) to a tooth brace for the purpose of realigning malocclusions. In other embodiments, the T-shaped bar (501) may be adjusted horizontally and/or the orthodontic screw (104) may be repositioned vertically within the slot (504) at the bottom of the T-shaped bar (501) in order to guide the realignment process.

In another embodiment, the T-shaped bar may contain a C-shaped rail on its lower portion (505) and a nut (205) may be inserted into either end, shifted horizontally from end to end and fixed by inserting an orthodontic screw (104) through the opening between the horizontal extensions at the top of the C-shaped rail and tightened with sufficient pressure as understood in the skill of the art.

As shown in FIG. 1, a self-tapping bone anchorage screw (101) maintains an elongated optionally hexagonal head (102) with internal threading 103. An orthodontic screw (104) with the same sized head (105) is inserted through a slot (302) on a rail bar (301) or T-shaped bar (501) and set into the elongated head (102) of the bone anchorage screw (101). The bone anchorage screw head (102) and the orthodontic screw head (105) is preferably the same shape and size in order to maintain quickness and ease of use in the installation process. The orthodontic screw head (105) also maintains an indentation (106) in its head wherein linking materials (801) such as elastic bands or metal wires may be wrapped around it and be used to fixate the maxilla and mandible.

Figure 2:
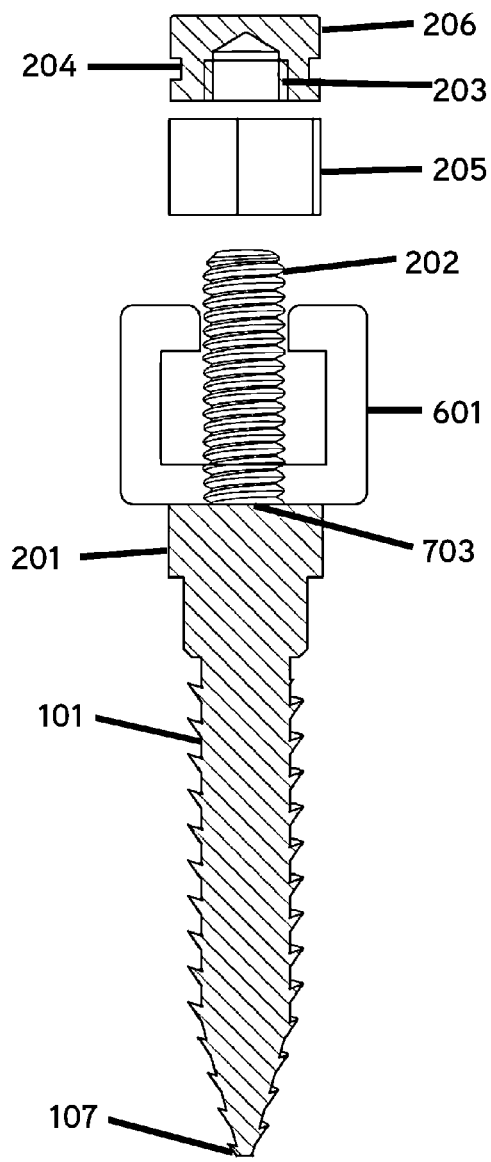
FIG. 2 is a side and cross-sectional view of another exemplary embodiment of the bone anchorage screw (101) with a screw (202) extending from its head inserted into a hole in one embodiment of a rail bar (601). A nut (205) and/or cap nut (206) with a horizontal indentation (204) to be set to said screw extension (202).

As shown in FIG. 2, a bone anchorage screw (101) maintaining a short head (201) with an externally threaded extension (202). The externally threaded screw end (202) is inserted through a slot (703) on the bottom of a C-shaped rail bar (601) or T-shaped bar (501) and is fixed to the bar (301) using a nut (205) that is the same size as the head (201) of the screw (101). The nut may be a simple nut 205 with internal threading that passes through, or it may be a capped nut (206) with internal threading (203) that does not pass through it and that maintains an indentation (204) that may act as an anchor point for IMF or protection from gum tissue that may potentially be affected by the externally threaded screw (202) passing through it.

The bone anchorage screw (101) is to be inserted completely into the bone tissue until it reaches the optionally hexagonal head (102/201) which provides sufficient distance to prevent a rail bar (601) or T-shaped bar (501) from touching the gingiva or mucosa.

Insertion of the bone anchorage screw (101) is preferably located at a sufficient distance from dental roots in order to avoid damaging the root or sensitive nerves in the region. It is desired that the screw (101) not be inserted between teeth roots.

FIG. 3 shows a flat rail bar (301). The rail bar (301) is flexible and can be molded to the contours of the maxilla or mandible according to its placement. It contains rounded corners and edges (401), which provide for patient comfort. The rail bar (301) contains a plurality of slots (302) for fixating to bone anchorage screws (101) or attaching modular items such as orthodontic screws (104) or T-shaped bars (501). The rail bar (301) may be shifted horizontally or an attachment to the rail bar (301) may be shifted horizontally according to the necessary placement in order to achieve the highest accuracy in fixation or realignment of the maxilla, mandible or teeth. It may be made of any material that may produce a sanitary environment within the mouth, including but not limited to metal—titanium, stainless steel, or aluminum, plastic, or silicon.

FIG. 4 is an end view of a flat rail bar (301) that illustrates an exemplary curvature of its edges (401).

FIG. 5A illustrates a T-shaped bar (501) that can be used for a multitude of purposes. It is defined by two wings (502) that form the head of the T, each side with one hole (503) that can be used to attach it to a rail bar (301) or other T-shaped bar (501). The bottom of the T contains an elongated space (504) that allows for easily repositioning and/or adjusting the T-shaped bar (501) or any attachment to it, such as an orthodontic screw (104), in a vertical position.

FIG. 5B illustrates an embodiment of a T-shaped bar (501) in which the bottom portion (505) is a C-shaped rail bar, allowing for a nut (205) to be inserted in either end and shifted vertically from one end to the other.

Figure 6:
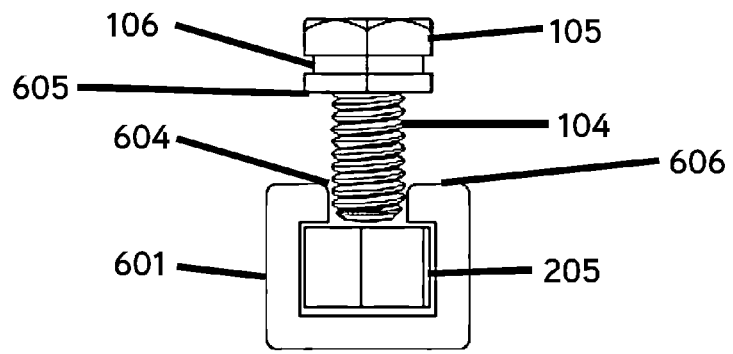
FIG. 6 is a side view of an orthodontic screw (104) being placed through a C-shaped rail bar (601) that is then set with a nut (205).

FIG. 6 shows how an orthodontic screw (104) which is to be set to a C-shaped rail bar (601) via a nut (205) inserted within the C. Once the nut (205) has been inserted into the C-shaped rail bar (601) through one of the side openings (701) or from the end of the rail bar (702), it can only be shifted horizontally from one end of the rail bar (601) to the other. This allows for a nut (205) to be set in such a way that an orthodontic screw (104) may be inserted and the nut (205) will not turn. After the nut (205) has been set into its desired position, an orthodontic screw (104) with the same size head (105) as the nut (205), is inserted through the top opening (604) of the C-shaped rail bar (601) and into the nut (205) and turned until the bottom of the head (605) touches the top (606) of the C-shaped rail bar (601) and is fixed with sufficient pressure as is understood in the skill of the art. This orthodontic screw (104) may also pass through an opening (302) on another rail bar (301) or T-shaped bar (501) or other modular extension with a hole before entering the nut (205) and being fixed. The orthodontic screw (104) maintains an indentation (106) in its head (105) where a linking material (801) such as elastic bands or metal wires may be wrapped around it another screw head, allowing for IMF or for dental realignment.

Figure 7:
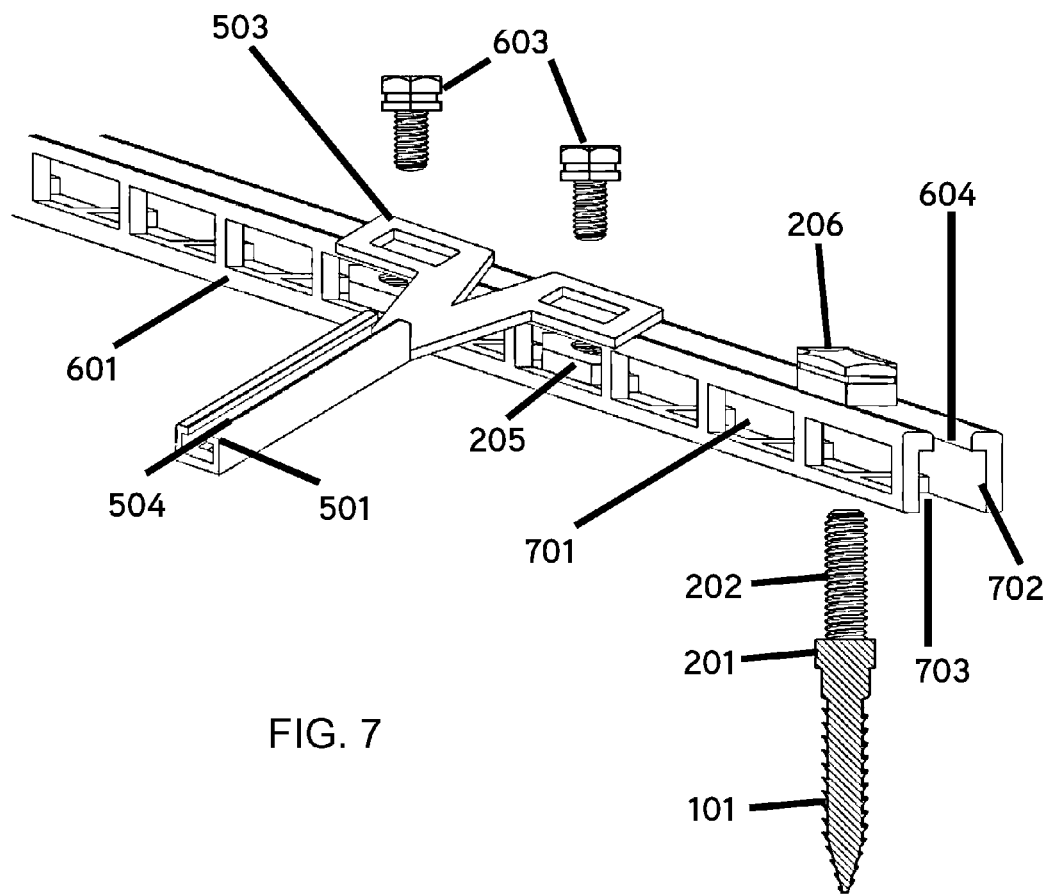
FIG. 7 is a top isometric view of a C-shaped rail bar (601) that is being set to a bone anchorage screw (101) with an extended screw head (202) and a T-shaped orthodontic bar (501) being set to the C-shaped rail bar (601) according to one embodiment.

FIG. 7 shows various steps in the positioning of the C-shaped rail bar (601) onto the bone anchorage screw (101) with the externally threaded screw (202) extending from its head showed in the FIG. 2 and the T-shaped bar (501) onto the C-shaped rail bar (601). Once the bone anchorage screw (101) has been set into the bone issue until its head (201) sits firmly on the bone tissue and is surrounded by gingiva or mucosa. The externally threaded screw (202) extending from the head (201) is set through one of the multitude of slots (703) on the bottom of the C-shaped rail (601) bar and passed through the opening (604) at the top of the C, where it is then fixed with a cap nut (206) using the appropriate tightness as is understood by someone with skill in the art. For setting a T-shaped bar (501) along the C-shaped rail bar (601), nut(s) (205) are to be inserted in the side openings (701), as is described in FIG. 6, a T-shaped bar (501) is laid over the C-shaped bar (601) and an orthodontic screw (104) is inserted through at least one of its three slots (503, 504), passed through the opening (604) at the top of the C-shaped bar (601), and fixed with the appropriate tightness to the nut (205) as is understood by someone with skill in the art.

Figure 8:
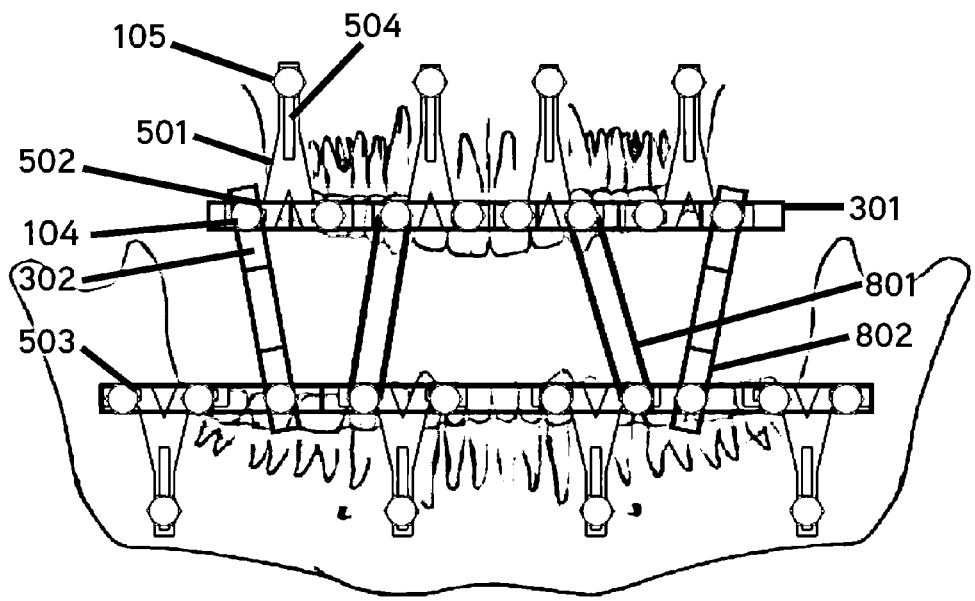
FIG. 8 is a front view of the system of the present invention being used in a patient's mouth for an intermaxillary fixation.

FIG. 8 shows the complete system being used for IMF. The T-shaped bars (501) are flexible and may be molded to the vertical maxilla contour with the head of the T (502) floating over the teeth. They may also be molded horizontally due to the V-shaped cut in the head of the T (502), thereby creating wings that can form the lateral contour of the maxilla. The bottom of the T-shaped bars (504) are fixed to the bone anchorage screws (101) using orthodontic screws (104) (as is described in FIG. 1) or a nut (206) (as is described in FIG. 2). The head (502) of the T-shaped bar (501) should be aligned horizontally with each other in order to produce ease in setting a rail bar (301) over them. A rail bar (301) should then be bent to conform to the contours of the maxilla or mandible prior to being set, however, it can also be bent during the placement process. A flat rail bar (301) may be attached over the heads (502) of the T-shaped bars (501) and fixed using orthodontic screws (104) placed through a slot (302) on the rail bar (301) and through a slot (503) on the T-shaped bar (501) and fixed below with a nut (205). A C-shaped rail bar (601) may also be attached over the heads (502) of the T-shaped bars (501) as is described in FIG. 7.

Once the rail bars (301/601) have been set to the heads (502) of the T-shaped bars (501), wires or elastic bands (801) may be wrapped around the head (105) of the orthodontic screws (104) or nuts (206) located on the maxilla and mandible that contain an indentation (204/106) for receiving the wires or elastic bands (801).

For edentulous patients, a rail bar extension (802) may be attached to both the maxilla and mandible rail bars (301/601), setting an appropriate distance as is understood in the skill of the art between the two before fixing the rail bars (802) with the orthodontic screws (104) and nuts (205). This practice may also be used for non-edentulous patients and maintains a more secure IMF.

By placing the bottom of the T-shaped bar (501) on the bone anchorage screws (101), it is possible for the bone anchorage screws (101) to avoid any dental or nerve damage by being placed too close to the roots while also extending the rail bar (301/601) away from the surgical space in order to avoid conflict with the rail bar (301/601). This allows for fixation without touching the teeth, teeth roots, or gingiva, allowing the patient to easily clean their mouth and avoiding any possible periodontal or gingival disease during the IMF period.

Figure 9:
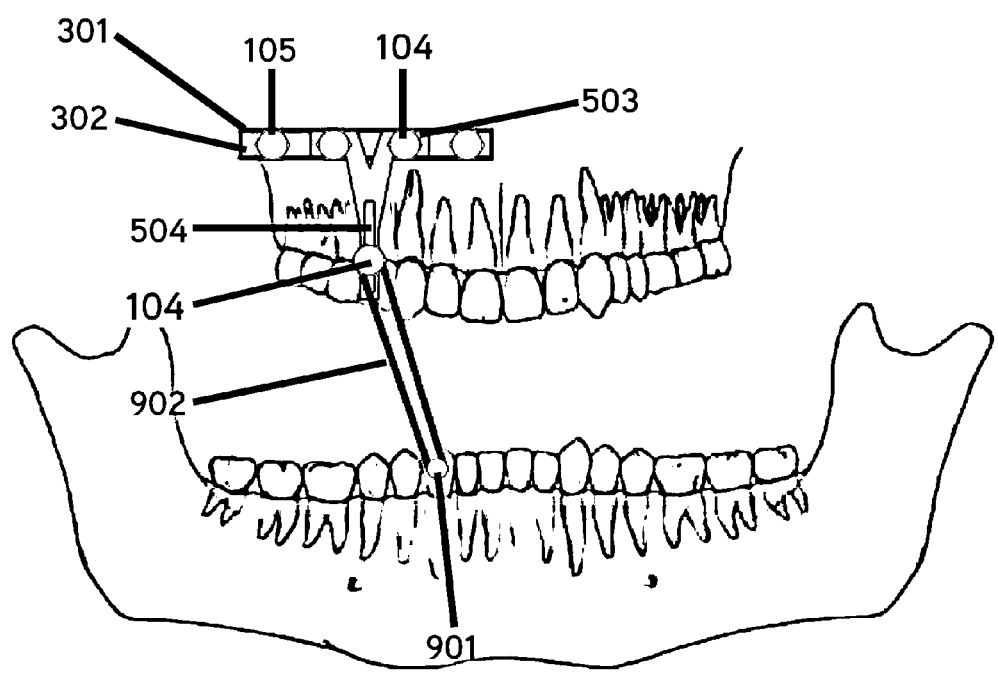
FIG. 9 is a front view of the system of the present invention using the T-shaped orthodontic bar (501) being used in a patient's mouth for a tooth realignment.

In FIG. 9, the system has been manipulated to work for dental realignment for malocclusions. A rail bar (301/601) has been attached to a minimum of two bone anchorage screws (101), the head (502) of a single T-shaped bar (501) has been attached with orthodontic screws (104) and nuts (205) placed through the slots (503) on its wings (502) and into the rail bar (301/601) in its desired position and an orthodontic screw (104) is set with a nut (205) to the desired position within the slot (504) at the bottom of the T (501). The T-shaped bar (501) may be repositioned throughout the realignment process by loosening the nuts (205), repositioning the T-shaped bar (501) horizontally along the rail bar (301/601), and fixing the nuts (205) again. The position of the orthodontic screw (104) may be repositioned throughout the realignment process by loosening the nut (205), repositioning the orthodontic screw (104) vertically and fixing it again by tightening the nut (205).

Once the rail bar (301/601), T-shaped bar (501), and orthodontic screws (104) have been placed in their desired position, wires or elastic bands 902 are then wrapped around the indentation (106) in the head (105) of the orthodontic screw (104) and then to a brace attached to the tooth (901).

What is claimed is:

1. An intermaxillary fixation and dental realignment system comprising:
    a bone anchorage screw comprising at least one of an elongated head with internal threading and an externally threaded screw extending from a head of said bone anchorage screw;
    a fixation system;
    a rail bar; and
    a T-shaped bar coupled to the rail bar;
    wherein the T-shaped bar comprises an elongated slot positioned on a vertical leg of the T that accommodates at least one of an orthodontic screw and the bone anchorage screw;
    wherein the T-shaped bar further comprises one or more elongated slots positioned on a horizontal top portion of the T that accommodate at least one of an orthodontic screw and the bone anchorage screw;
    wherein the fixation system comprises an internally threaded nut that fixates the externally threaded screw extending from the head of said bone anchorage screw;
    wherein the internally threaded nut comprises at least one of a nut and a capped nut; and
    wherein the at least one of the nut and the capped nut has an indentation for receiving linking materials, wherein the indentation extends around an entire circumference of the nut or the capped nut.

2. The system of claim 1, wherein the rail bar comprises a C-shaped rail bar.

3. The system of claim 1, wherein the rail bar is flat, flexible and has rounded edges.

4. The system of claim 1, wherein the T-shaped bar has a C-shaped rail at a bottom of the T.

5. The system of claim 1, comprising a plurality of rail bars coupled to bone anchorage screws and coupled to one or more T-shaped bars via orthodontic screws and/or nuts and/or cap nuts.

6. The system of claim 1, wherein the bone anchorage screw fixates at least one of the T-shaped bar and the rail bar.

7. The system of claim 1, wherein one or more orthodontic screws couple the T-shaped bar to the rail bar.

8. The system of claim 1, wherein the T-shaped bar is flexible and has rounded edges.

9. The system of claim 1, wherein the elongated slots positioned on the horizontal top portion of the T accommodate one or more orthodontic screws for adjustable attachment to the rail bar.

10. The system of claim 1, wherein the elongated slot positioned on the vertical leg of the T accommodates one or more bone anchorage screws for adjustable attachment to a jaw bone.

* * * * *